(12) United States Patent
Hendel

(10) Patent No.: US 6,410,308 B2
(45) Date of Patent: Jun. 25, 2002

(54) DEVICE FOR EXAMINING THE STERILITY OF FLUIDS

(76) Inventor: Jens Hendel, Frohngartenweg 8, D-76189 Karlsruhe (DE)

( * ) Notice: Subject to any disclaimer, the term of this patent is extended or adjusted under 35 U.S.C. 154(b) by 0 days.

(21) Appl. No.: 09/818,852

(22) Filed: Mar. 28, 2001

(30) Foreign Application Priority Data

Mar. 30, 2000 (DE) .......................................... 100 15 788

(51) Int. Cl.⁷ ................................................. C12M 1/34
(52) U.S. Cl. ............................... 435/287.4; 435/288.1; 435/288.2; 435/288.6
(58) Field of Search ........................... 435/287.1, 287.4, 435/288.1, 288.2, 288.6

(56) References Cited

U.S. PATENT DOCUMENTS

| | | | |
|---|---|---|---|
| 5,340,741 A | * | 8/1994 | Lemonnier .................. 435/291 |
| 5,554,536 A | | 9/1996 | Rising |
| 5,593,587 A | | 1/1997 | Fumihiko |

FOREIGN PATENT DOCUMENTS

| | | |
|---|---|---|
| DE | 1 611 043 | 10/1970 |
| DE | 7 413 669 | 9/1974 |
| DE | 298 03 712 | 6/1998 |
| DE | 198 23 993 | 12/1999 |
| DE | 198 23 994 | 12/1999 |
| EP | 05 57 041 | 8/1993 |
| EP | 0 818 540 | 1/1998 |
| WO | WO87/00 858 | 2/1987 |
| WO | WO99/47 637 | 9/1999 |

* cited by examiner

*Primary Examiner*—David A. Redding
(74) *Attorney, Agent, or Firm*—Paul Vincent

(57) ABSTRACT

A device for examining the sterility of fluids, in particular of pharmaceutical products is proposed. The device comprises a diaphragm filter inserted into a filtering unit for sterile filtration of the fluid, a collecting container which can be connected with the outlet of the filtering unit for the filtered matter and a container receiving at least one nutrition medium for incubation of the diaphragm filter to detect microorganisms. In accordance with the invention, the diaphragm filter can be inserted into and removed from the filtering unit by means of a handling device and be transferred by same, without contact, into the container receiving the nutrition medium such that, before incubation of the diaphragm filter, contamination of the diaphragm filter and of the nutrition medium is largely prevented to suppress erroneous positive results. The diaphragm filter preferably comprises a large surface and is substantially cylindrical, conical or tapered.

18 Claims, 2 Drawing Sheets

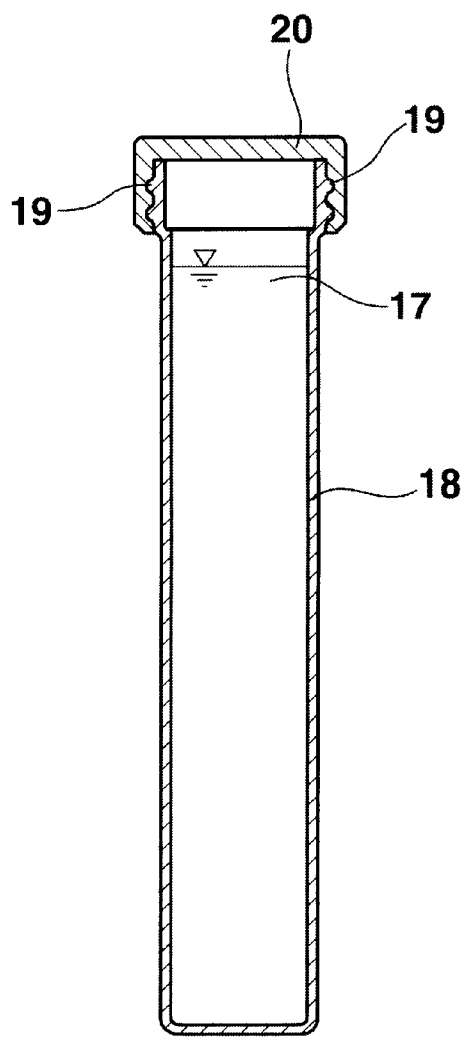
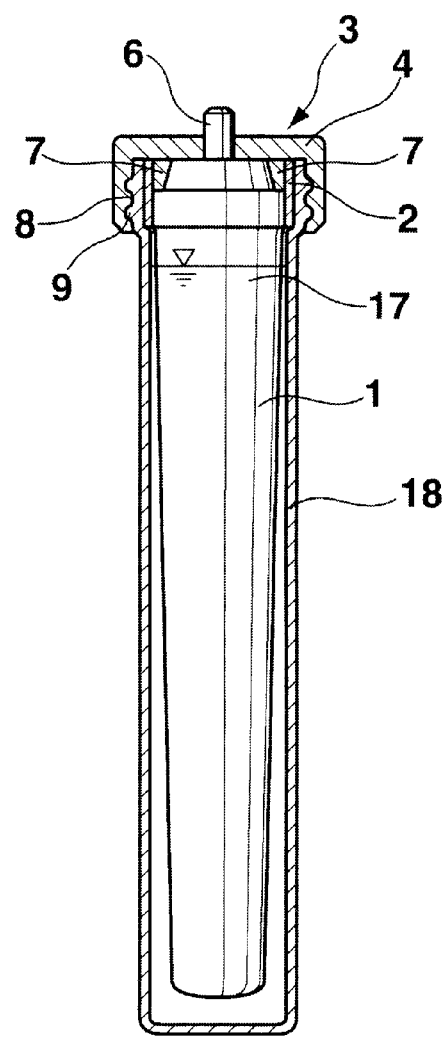
Fig. 2  Fig. 3

DEVICE FOR EXAMINING THE STERILITY OF FLUIDS

This application claims Paris Convention priority of DE 100 15 788.2 filed Mar. 30, 2000 the entire disclosure of which is hereby incorporated by reference.

BACKGROUND OF THE INVENTION

The invention concerns a device for examining the sterility of fluids, in particular pharmaceutical products, comprising a diaphragm filter for sterile filtering of the fluid, which is inserted into a filtering unit, a collecting container for the filtered matter, which can be connected to an outlet of the filtering unit, and a container receiving at least one nutrition medium to incubate the diaphragm filter for detecting microorganisms.

To examine the sterility of fluids which have to meet the highest hygienic standards, e.g. liquid, emulsified or dissolved pharmaceutical substances, active substances or the like and other filterable products, the fluid is usually filtered by means of a diaphragm filter which is impermeable to microorganisms and the diaphragm filter is subsequently incubated in a nutrition medium which, in case of microbial contamination of the fluid, produces an increase in the microorganisms accumulating on the filter. The propagation of microorganisms can be monitored and documented permanently or at regular time intervals thereby permitting qualitative detection of the microbial contamination of the test medium. The diaphragm filter is optionally washed before incubation in the nutrition medium to exclude any errors in the determined bacterial count caused by different fluid matrices, e.g. fluids having different antibiotic and consequently bacterial growth-blocking effects. The diaphragm filter must have a pore width of less than 0.45 $\mu$m in accordance with the required guidelines, e.g. the current pharmacopoeias, to guarantee retainment of the microorganisms on the filter. A similar approach is used in water technology for determining the bacterial count of water, e.g. drinking water, tap water, ground water, surface water, waste water or the like and in food technology.

Devices for sterile filtering of fluids are known which comprise a filtering unit which can be mounted onto a collecting container for the filtered matter and into which a diaphragm filter can be inserted which is usually designed as an annular disc. The fluid is supplied to the diaphragm filter by applying an underpressure to the collecting container which is designed e.g. like a suction bottle or by applying an overpressure on a reservoir connected to the filtering unit and accommodating the fluid to be examined. After sterile filtering, the diaphragm filter is manually transferred into a container having the nutrition medium, e.g. via a pair of tweezers, the container is closed and incubated at a predetermined temperature for a predetermined time. The replication of the microorganisms retained on the filter, which occurs in case of microbial contamination of the fluid, is usually visually assessed by the cloudiness of the medium accompanying bacterial growth. Disadvantageously, the complicated handling of the diaphragm filter does not permit automatic examination of a plurality of samples, and the free handling of the diaphragm filter, in particular during transfer of the filtering unit into the nutrition medium, risks contamination from the surroundings which can lead to erroneous positive results.

Moreover, closed devices comprising several filtering units, each accommodating one diaphragm filter, and a pump connected therewith are known. The fluid to be examined, an optional wash solution, and the nutrition solution are successively supplied to the diaphragm filters by means of the pump. When the filtering units are filled with the nutrition solution, thereby wetting the diaphragm filter, the filtering units are closed, removed from the device and incubated to assess bacterial growth in case of microbial contamination of the fluid. Although this largely prevents subsequent contamination of the diaphragm filter, the device is demanding and expensive.

It is the underlying purpose of the invention to further develop a device of the initially mentioned type in a simple and inexpensive fashion such that reproducible results are obtained and erroneous positive results are reliably prevented.

SUMMARY OF THE INVENTION

In accordance with the invention, this object is achieved in a device of the initially mentioned type in that the diaphragm filter can be inserted into and removed from the filtering unit by a handling device and be moved without contact into the container containing the nutrition medium by the same handling device.

The inventive handling device largely prevents contact between the diaphragm filter and the surroundings, in particular when removing the diaphragm filter from the filtering unit and moving same into the nutrition solution, thereby reliably preventing external contamination of the diaphragm filter which would lead to erroneous positive results. The inventive device permits a substantially sterile transfer of the diaphragm filter into the container holding the nutrition medium. The container may be advantageously designed as a measuring unit for automatic detection of microbial growth, which is particularly advantageous with large numbers of samples. Such automatic detection of the microorganism growth, e.g. through continuous or regular measurement of its metabolic products, such as carbon dioxide, eliminates the conventional visual assessment of the medium which requires substantial time and personnel. The device can be universally applied for different sample volumes and pore sizes of the diaphragm filter. The handling device is preferably integrated in the diaphragm filter.

In a preferred embodiment, the handling device comprises a cap with a filler neck for the fluid to be filtered, the wash solution, or the like, which can be mounted on the filtering unit and also on the container receiving the nutrition medium. In this fashion, the diaphragm filter can be removed from the filtering unit after sterile filtration of the fluid to be examined and optional washing, and be disposed on the container receiving the nutrition medium for incubation, thereby wetting the diaphragm filter with the nutrition medium. To seal the container receiving the nutrition medium with the diaphragm filter during incubation, the filler neck of the cap can be tightly sealed e.g. by means of a stopper.

In a preferred embodiment, a screw connection is provided between the handling device of the diaphragm filter and the filtering unit as well as on the container receiving the nutrition medium in order to provide a sealing connection between the handling device receiving the diaphragm filter and the filtering unit or the container accommodating the nutrition medium, which can be easily closed and opened.

The connection between the diaphragm filter and the handling device is preferably a releasable connection e.g. a plug connection or a weakened region, in particular a breaking point which can preferably be manually released by means of an actuator disposed on the handling device. A handling device of this type which is integrated in the diaphragm filter and connected therewith via a releasable connection, e.g. a breaking point, guarantees fundamental sterility, wherein the entire unit may be sealed, in particular by the manufacturer, to preclude external contamination of the diaphragm filter. In this fashion, the cap of the handling device can be removed from the filtering unit after sterile filtering and optional washing of the filter and the diaphragm filter can be removed from the filtering unit by means of the handling device connected therewith and disposed onto the container receiving the nutrition medium for incubation. Manual triggering of the actuator of the handling device releases same from the diaphragm filter along the breaking point causing the diaphragm filter to fall into the nutrition solution of the incubation container to be rinsed by the nutrition solution on its inner and outer side. Subsequently, the container may be closed and incubated by means of a lid integrated e.g. in the handling device.

The diaphragm filter is preferably either substantially cylindrical or substantially slightly conical or truncated and connected to the handling device at an open end face, wherein the connection between the diaphragm filter and the handling device can preferably be released, as mentioned above, and designed e.g. as a breaking point or plug connection. A diaphragm filter designed in this fashion has a considerably larger surface for retaining and collecting microorganisms from the sample medium compared to that of conventional diaphragm filters, designed as annular discs, which, in the subsequent test, permits an improved flow of microorganisms through the nutrition medium and therefore improved measuring accuracy and reproducibility, while thereby preventing erroneous positive results.

To prevent back-flow of the filtered matter from the collecting container (which is usually not sterile) into the coupled filtering unit and thereby contamination of the diaphragm filter, a preferred embodiment provides for disposition of a retaining means for the filtered matter in the collecting container in the region of the outlet of the filtering unit and/or in the region of an intake of the collecting container, which can be connected therewith. The retaining means may be formed e.g. like a bacteria-tight filter, in particular a diaphragm filter or a valve, such as a check valve.

Preferably, a plug connection, e.g. a nozzle is provided between the filtering unit and the collecting container, wherein e.g. the filtering unit comprises, at its lower side, a centering projection, surrounding the outlet, for mounting to a holding projection formed on the upper side of the collecting container or on a lid of same. This ensures that the outlet of the filtering unit tightly abuts an intake disposed at the upper side of the collecting container or on its lid when the filtering unit is mounted on the collecting container.

The device in accordance with the invention is furthermore preferably autoclavable.

The invention is described in more detail below by means of a preferred embodiment and with reference to the drawing.

BRIEF DESCRIPTION OF THE DRAWING

FIG. 2 shows a section of the container, receiving th e nutrition medium, of the device in accordance with FIG. 1; and FIG. 3 shows the container in accordance with FIG. 2 after inserting the diaphragm filter for incubation of the diaphragm filter.

DESCRIPTION OF THE PREFERRED EMBODIMENT

Figure 1:
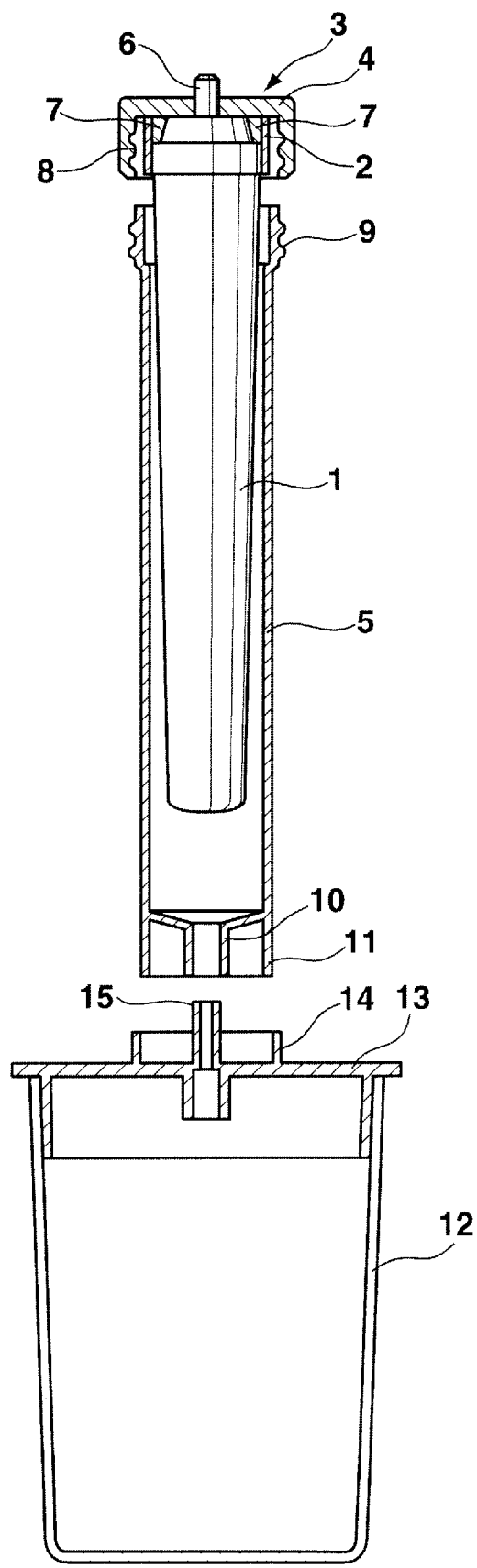
FIG. 1 shows an exploded view of a section of the embodiment, with filtering unit.

The device in accordance with FIG. 1 comprises a filtering unit 5 having a diaphragm filter 1, e.g. a nitrate acetate filter having a pore width of 0.45 $\mu$m which is shaped like a truncated cone or as slightly tapered cylinder, whose open end face 2 comprises a handling device 3 designed as cap 4. Towards this end, an inner side of the cap 4 has an annular collar 7 engaging into the open end face 2 of the diaphragm filter 1, which serves as a plug connection. The plug connection can be released by means of a manual actuator disposed on the cap 4, e.g. in the manner of an ejector. Alternatively, a weakened region, e.g. a breaking point can be provided between the handling device 3 and the diaphragm filter 1, which can be destroyed e.g. manually with little force by means of an actuator disposed on the handling device 3.

The cap 4 further comprises a filler neck 6 for introducing the test fluid to be filtered and an inner thread 8 which corresponds with an external thread 9 disposed on the upper side of the filtering unit. The cap 4 comprising the diaphragm filter 1 is already screwed onto the filtering unit 5 by the manufacturer and the entire unit is packed in a sterile fashion.

At its lower side, the filtering unit 5 comprises an outlet 10, which can be connected to a collecting container 12, for the sterile filtered fluid and having a centering projection 11 concentric with the outlet 10 by means of which the filtering unit 5 can be mounted to a holding projection 14 formed on the lid 13 of the collecting container 12. When placing the filtering unit 5 onto the cap 13 of the collecting container 12, the outlet 10 of the filtering unit 5 extends past an intake 15 disposed on the lid 13 thereby sealing same tightly.

For sterile filtration of the fluid to be examined, a pump can be connected either to the collecting container 12, formed like a suction bottle, or to the filler neck 6 of the cap 4 as a pressure pump. Moreover, a retaining means for the filtered matter located in the collecting container 12, in the form of a bacteria filter, a check valve or the like is disposed in the region of the outlet 10 of the filtering unit 5 or in the region of the intake 15 of the lid 13 of the collecting container 12.

FIG. 2 shows a container 18 accommodating the nutrition medium 17 for incubation of the diaphragm filter 1 (FIG. 1) to detect microorganism growth after sterile filtering of the fluid and optional washing of the diaphragm filter. The container 18 comprises an external thread 19 which corresponds to the external thread 9 of the filtering unit 5 (FIG. 1) and is closed by a lid 20. In this fashion, the diaphragm filter 1 can be moved without contact from the filtering unit 5 (FIG. 1) into the container 18 after removing the lid 20, using the handling device 3 formed as cap 4, to minimize contact between the diaphragm filter 1 and its surroundings and thus the possibility of contamination of the diaphragm filter 1, which would lead to erroneous positive results.

FIG. 3 shows the container 18 in accordance with FIG. 2 after transfer of the diaphragm filter 1 by the handling device 3, formed as cap 4, whose internal thread 8 is screwed onto the external thread 9 of the container 18. For incubation of the diaphragm filter, in particular when the diaphragm filter 1 and the handling device 3 are rigidly connected, the filler neck 6 of the cap 4 can be closed by a stopper. In the case of the releasable plug connection shown, the diaphragm filter 1 can be released from the handling device 3 through triggering the actuator of the handling device 3 and the container 18 comprising the diaphragm filter 1 can be closed by the lid 20 (FIG. 2). In any case, the large surface of the elongated diaphragm filter 1 provides good flow of the propagating microorganisms located on the filter 1 through the nutrition medium 17 and subsequent high measuring sensitivity and reproducibility.

The handling device 3, the filtering unit 5, the collecting container 12 and the container 18 receiving the nutrition medium 17 can preferably be autoclaved and are made e.g. from plastic material.

To examine the sterility of fluids, e.g. pharmaceutical products, the filtering unit 5 is mounted on the collecting container 12 and the fluid is filtered in a sterile manner by means of a pump. After sterile filtration, the diaphragm filter 1 is washed with a wash solution. The filtered matter located in the collecting container 12 is disposed of.

The diaphragm filter 1 is then removed without contact from the filtering unit 5 by means of the cap 4 and placed into the container 18, containing the nutrition medium 17, for incubation. The cap 4 comprising the diaphragm filter 1 is mounted onto the container 18 and either the filler neck 6 is tightly closed during incubation or, after mounting, the cap 4 is removed from the diaphragm filter 1 by an ejector or the like such that the inner and outer sides of the diaphragm filter 1 are wet with the nutrition medium 17 and the container 18 is tightly closed by the lid 20. Replication of microorganisms is detected in particular through continuous measurement and recording of their metabolic product content, e.g. carbon dioxide, in the nutrition medium 17 or in the gas blanket above the nutrition medium 17 in the container 18.

The fluid may e.g. be divided, before sterile filtration and in a manner known per se, into at least two identical volumes and each volume may be filtered by one separate diaphragm filter 1. In this case, the diaphragm filters 1 can be incubated in different nutrition media 17 and/or different conditions, e.g. aerobic/anaerobic, after sterile filtration of the equal fluid volumes.

| List of Reference Numerals | |
|---|---|
| 1 | diaphragm filter |
| 2 | open end face of the diaphragm filter |
| 3 | handling device |
| 4 | cap |
| 5 | filtering unit |
| 6 | filler neck |
| 7 | annular collar |
| 8 | internal thread |
| 9 | external thread |
| 10 | outlet |
| 11 | centering projection |
| 12 | collecting container |
| 13 | lid |
| 14 | holding projection |
| 15 | intake |
| 17 | nutrition medium |
| 18 | container |
| 19 | external thread |
| 20 | lid |

I claim:

1. A device for examining the sterility of fluids and pharmaceutical products, the device comprising:
    a filtering unit having an outlet;
    a diaphragm filter inserted into said filtering unit for sterile filtration of the fluid;
    a first container having intake means for connection to said outlet of said filtering unit to collect filtered fluids;
    a second container for receiving and holding at least one nutrition medium; and
    means for handling said diaphragm filter for inserting and removing said diaphragm filter into and from said filtering unit and for placing, without contact, said diaphragm filter into said second container to incubate said diaphragm filter with the nutrition medium, to detect microorganisms.

2. The device of claim 1, wherein said handling means is integral with said diaphragm filter.

3. The device of claim 1, wherein said handling means comprises a cap for placement on said filtering unit and for placement on said second container receiving the nutrition medium, said cap having a filler neck for the fluid to be filtered.

4. The device of claim 3, further comprising means for closing said filler neck of said cap.

5. The device of claim 1, wherein said handling means, said filtering unit, and said second container each have a cooperating screw connection.

6. The device of claim 1, wherein one of said handling means and said diaphragm filter comprises means for releasable connection of said handling means to said diaphragm filter.

7. The device of claim 6, wherein said releasable connection means between said diaphragm filter and said handling means comprises a plug connection.

8. The device of claim 6, wherein said means for releasable connection between said diaphragm filter and said handling means is one of a weakening line and a breaking point.

9. The device of claim 6, wherein said handling means comprises actuator means cooperating with said releasable connection means.

10. The device of claim 1, wherein said diaphragm filter is substantially cylindrical and is connected, at an open end face thereof, to said handling means.

11. The device of claim 1, wherein said diaphragm filter is one of substantially conical and shaped as a truncated cone and is connected, at an open end face thereof, to said handling means.

12. The device of claim 1, further comprising means for retaining filtered fluids in said first container, said retaining means disposed in a region of said outlet of said filtering unit.

13. The device of claim 1, further comprising means for retaining filtered fluids in said first container, said retaining means disposed in a region of said intake means of said first container.

14. The device of claim 12, wherein said retaining means is one of a bacteria-tight filter, a diaphragm filter, a valve means, and a check valve means.

15. The device of claim 13, wherein said retaining means is one of a bacteria-tight filter, a diaphragm filter, a valve means, and a check valve means.

16. The device of claim 1, wherein said filtering unit and said first container have a plug connection.

17. The device of claim 16, wherein said filtering unit has a centering projection at a lower side thereof which surrounds said outlet, said centering projection for mounting onto a holding projection formed on an upper side of said first container or in a lid thereof, wherein, when mounting said filtering unit on said first container, said outlet of said filtering unit tightly abuts said intake means disposed on said upper side of said first container or on said lid thereof.

18. The device of claim 1, wherein said device is constructed for treatment in an autoclave.

* * * * *